(12) United States Patent
Brauer et al.

(10) Patent No.: US 9,022,931 B2
(45) Date of Patent: May 5, 2015

(54) INTERFACE FOR A HEALTH MEASUREMENT AND MONITORING SYSTEM

(75) Inventors: Jacob Brauer, Chicago, IL (US); Darren Brown, Harrison, NY (US); Jun Chen, Warren, NJ (US); Richard Kates, Ridgewood, NJ (US); Jennifer M. Levin, Chicago, IL (US); Harris Lieber, White Plains, NY (US); Amy Schwartz, Evanston, IL (US); Raymond Yao, Tarrytown, NY (US)

(73) Assignee: Bayer HealthCare LLC, Whippany, NJ (US)

( * ) Notice: Subject to any disclaimer, the term of this patent is extended or adjusted under 35 U.S.C. 154(b) by 1309 days.

(21) Appl. No.: 12/156,043

(22) Filed: May 29, 2008

(65) Prior Publication Data

US 2009/0149717 A1    Jun. 11, 2009

Related U.S. Application Data

(60) Provisional application No. 61/012,721, filed on Dec. 10, 2007, provisional application No. 61/012,718, filed on Dec. 10, 2007.

(51) Int. Cl.
*A61B 5/00* (2006.01)
*G06F 19/00* (2011.01)

(52) U.S. Cl.
CPC ........ *G06F 19/3406* (2013.01); *G06F 19/3456* (2013.01); *G06F 19/3487* (2013.01)

(58) Field of Classification Search
USPC .............. 600/300–301, 365; 702/19; 435/14; 604/67; 705/2–4
See application file for complete search history.

(56) References Cited

U.S. PATENT DOCUMENTS

| 5,019,974 A | 5/1991 | Beckers ................. 364/413.02 |
| D363,885 S | 11/1995 | Okamoto et al. ............. D10/78 |

(Continued)

FOREIGN PATENT DOCUMENTS

| CN | 200953023 | 9/2007 | ............ A61B 5/145 |
| CN | 101080718 | 11/2007 | ............... A61B 5/00 |

(Continued)

OTHER PUBLICATIONS

Accu-Chek® Complete Blood Glucose Monitoring System User's Manual, © 1997 Boehringer Mannheim Corporation, 97 pages.

(Continued)

*Primary Examiner* — William Thomson
*Assistant Examiner* — Bobby Soriano
(74) *Attorney, Agent, or Firm* — Nixon Peabody LLP

(57) ABSTRACT

A testing system and method for providing a testing system includes a user interface having a display for displaying information relating to measurements of health data and an input device for receiving information from a user relating to the health data. Provided in connection with the user interface is an autologging feature adapted to provide the user with user-selectable options on the display. Also provided is a statistical operation adapted to provide the user with enhanced information relating to the measurements of health data. Also provided is at least one indicator for indicating information relating to the number of health data readings that are within a target range, the number of health data readings that are above the target range and the number of health data readings that are below the target range.

13 Claims, 7 Drawing Sheets

(56) References Cited

U.S. PATENT DOCUMENTS

| | | | |
|---|---|---|---|
| 5,507,288 A | 4/1996 | Bocker et al. | 128/633 |
| 5,575,403 A | 11/1996 | Charlton et al. | 221/31 |
| D411,621 S | 6/1999 | Eisenbarth et al. | D24/169 |
| 6,246,966 B1 | 6/2001 | Perry | 702/91 |
| 6,519,141 B2 | 2/2003 | Tseng et al. | 361/683 |
| D493,536 S | 7/2004 | Jaeck et al. | D24/169 |
| D545,436 S | 6/2007 | Padain | D24/169 |
| D545,438 S | 6/2007 | Huang et al. | D24/186 |
| D546,216 S | 7/2007 | Bolognesi et al. | D10/81 |
| D546,454 S | 7/2007 | Gutmann et al. | D24/169 |
| 7,241,265 B2 | 7/2007 | Cummings et al. | 600/300 |
| 7,273,454 B2 * | 9/2007 | Raymond et al. | 600/301 |
| D581,056 S | 11/2008 | Kurokawa et al. | D24/169 |
| 7,467,065 B2 * | 12/2008 | Neel et al. | 702/183 |
| D590,063 S | 4/2009 | Garthoff et al. | D24/186 |
| D595,415 S | 6/2009 | Fukuzawa | D24/186 |
| D611,151 S | 3/2010 | Lei | D24/169 |
| 7,771,320 B2 * | 8/2010 | Riley et al. | 482/9 |
| 7,963,921 B1 * | 6/2011 | Freund et al. | 600/485 |
| 7,976,467 B2 * | 7/2011 | Young et al. | 600/365 |
| 2002/0002326 A1 * | 1/2002 | Causey et al. | 600/300 |
| 2003/0031591 A1 | 2/2003 | Whitson et al. | 422/50 |
| 2003/0176183 A1 | 9/2003 | Drucker et al. | 455/414.1 |
| 2003/0208110 A1 * | 11/2003 | Mault et al. | 600/300 |
| 2004/0048394 A1 | 3/2004 | Kirchhevel | 436/183 |
| 2004/0118704 A1 | 6/2004 | Wang et al. | 205/792 |
| 2005/0038674 A1 * | 2/2005 | Braig et al. | 705/2 |
| 2005/0086082 A1 | 4/2005 | Braunstein et al. | 705/2 |
| 2005/0143675 A1 | 6/2005 | Neel et al. | 600/583 |
| 2006/0293570 A1 * | 12/2006 | Croghan et al. | 600/300 |
| 2007/0021979 A1 * | 1/2007 | Cosentino et al. | 705/2 |
| 2007/0233395 A1 | 10/2007 | Neel et al. | 702/19 |
| 2007/0255123 A1 | 11/2007 | Cummings et al. | 600/309 |
| 2008/0015422 A1 | 1/2008 | Wessel | 600/301 |
| 2008/0058626 A1 * | 3/2008 | Miyata et al. | 600/365 |
| 2008/0071580 A1 * | 3/2008 | Marcus et al. | 705/3 |
| 2008/0133146 A1 | 6/2008 | Chang et al. | 702/23 |
| 2008/0139910 A1 * | 6/2008 | Mastrototaro et al. | 600/365 |
| 2008/0194987 A1 * | 8/2008 | Boecker | 600/583 |
| 2008/0252642 A1 | 10/2008 | Hansen et al. | 345/440 |
| 2008/0268485 A1 | 10/2008 | Guarino et al. | 435/14 |
| 2008/0275309 A1 * | 11/2008 | Stivoric et al. | 600/300 |
| 2008/0294024 A1 * | 11/2008 | Cosentino et al. | 600/309 |
| 2008/0306353 A1 * | 12/2008 | Douglas et al. | 600/301 |
| 2009/0030382 A1 | 1/2009 | Brandt et al. | 604/289 |
| 2009/0105570 A1 * | 4/2009 | Sloan et al. | 600/365 |
| 2009/0149729 A1 * | 6/2009 | Young et al. | 600/365 |
| 2009/0304547 A1 | 12/2009 | Werner et al. | 422/55 |

FOREIGN PATENT DOCUMENTS

| | | | |
|---|---|---|---|
| EP | 1369688 | 12/2003 | G01N 33/49 |
| EP | 1494158 | 1/2005 | G06F 19/00 |
| JP | 2003-520091 | 7/2003 | A61B 5/00 |
| JP | 2003-521972 | 7/2003 | A61B 5/00 |
| JP | 3658651 | 6/2005 | A61B 5/00 |
| RU | 2234238 | 8/2004 | A61B 10/00 |
| RU | 2285442 | 10/2006 | A61B 5/00 |
| WO | 01-28416 | 4/2001 | |
| WO | 2005-001680 | 1/2005 | |
| WO | 2005/040793 | 5/2005 | G01N 33/487 |
| WO | 2006/003181 | 1/2006 | G06F 19/00 |
| WO | 2006/066038 | 6/2006 | G06F 19/00 |
| WO | 2006/072035 | 7/2006 | A61B 5/00 |
| WO | 2006-123253 | 11/2006 | |
| WO | 2007-076540 | 7/2007 | |

OTHER PUBLICATIONS

TheraSense® FreeStyle Tracker Diabetes Management System Blood Glucose Testing Guide, © 2002 TheraSense, 17 pages.

OneTouch® UltraSmart Blood Glucose Monitoring System Meter and Electronic Logbook in One Owner's Booklet, © 2002 LifeScan, Inc., 69 pages.

Accu-Chek® Aviva Blood Glucose Meter Owner's Booklet © 2005 Roche Diagnostics, 80 pages.

OneTouch® Ultra® Blood Glucose Monitoring System Owner's Booklet, © 2005 LifeScan, Inc., 73 pages.

International Search Report and Written Opinion mailed Dec. 22, 2008 which issued in corresponding International Patent Application No. PCT/US2008/006813 (12 pages).

Extended European Search Report mailed Dec. 1, 2010 which issued in corresponding European Patent Application No. 10175004.0 (5 pages).

* cited by examiner

INTERFACE FOR A HEALTH MEASUREMENT AND MONITORING SYSTEM

CROSS-REFERENCE TO RELATED APPLICATION

This application claims the benefit of priority of U.S. Provisional Application Nos. 61/012,721 and 61/012,718, filed Dec. 10, 2007, which are hereby incorporated by reference in their entirety.

FIELD OF THE INVENTION

The present invention relates generally to systems and methods for the testing and monitoring of health data. More specifically, the systems and methods of the present invention provide an interface for displaying information regarding the testing and monitoring of health data in a more useful, efficient and intuitive manner.

BACKGROUND OF THE INVENTION

The quantitative determination of analytes in body fluids is of great importance in the diagnoses and maintenance of certain physiological conditions. For example lactate, cholesterol and bilirubin should be monitored in certain individuals. In particular, it is important that individuals with diabetes frequently check the glucose level in their body fluids to regulate the glucose intake in their diets. The results of such tests can be used to determine what, if any, insulin or other medication needs to be administered.

Diagnostic systems, such as blood-glucose systems, include a meter or instrument used to calculate a glucose value based on a measured output, such as current or color, and the known reactivity of the reagent-sensing element used to perform the test. Blood-glucose systems typically allow a user to collect a blood sample on a test sensor in which the test sensor is located in the meter. The meter measures the reaction between the glucose in the blood sample and a reagent from the test sensor to determine the blood-glucose concentration in the sample. These systems may store test results in the meter and may display the results to the user. A keypad or other interactive component may also be provided on a meter to allow a user to access the test results.

The user interface associated with these systems typically provide the user with certain features that relate to the testing results. For example, in some devices, the user enters information about the user's activities, including eating habits, exercise, etc. Typically, the user enters information after the testing has occurred and after the user has received the results. These systems are less effective at encouraging users to enter such information and in making the entering of the information an integral part of the testing process.

In view of the foregoing, there is a need for an approach that provides user interfaces that are simpler, more intuitive and that become an integrated part of the testing process. Systems that make the process of entering information about the user an easier, more intuitive process will provide the user with a better user experience and will ultimately give the user more accurate and meaningful information about his or her condition. Such systems will encourage users to provide information in such a manner that it will become a routine part of their testing regimen.

SUMMARY OF THE INVENTION

According to one embodiment, a testing system comprises a user interface including a display for displaying information relating to measurements of health data and an input device for receiving information from a user relating to the health data. The testing system further comprises an autologging feature adapted to provide the user with user-selectable options on the display and to prompt the user, during a time period corresponding to the amount of time needed to perform the measurements, to input information relating to the health data that corresponds to the appropriate user-selectable option.

According to another embodiment, a method of providing a testing system comprises the acts of providing the testing system having a user interface including a display, receiving health data of the user via a measurement system, and prompting the user to input user information that corresponds to the health data, such that the prompting occurs within a time period corresponding to the amount of time needed to perform measurements relating to the health data. The method further comprises performing the measurements relating to the health data and, during the performing of the measurements, receiving the user information that corresponds to the health data via an input device and displaying the measurements of the health data on the display.

According to a further embodiment, a testing system comprises a user interface including a display for displaying information relating to measurements of health data and an input device for receiving input from the user. The testing system also comprises a statistical operation adapted to provide the user with enhanced information relating to the measurements of health data. The statistical operation provides the user with an average value based on a plurality of health data readings determined for a specified time period. The testing system further comprises at least one indicator for indicating information relating to the number of health data readings that are within a target range, the number of health data readings that are above the target range and the number of health data readings that are below the target range.

In yet another embodiment, a method of providing a testing system comprises the acts of providing the testing system having a user interface including a display for displaying information relating to measurements of health data including a plurality of health data readings, receiving input from the user via the input device and performing a statistical operation to provide the user with enhanced information relating to the plurality of health data readings. The method further comprises displaying an output of the statistical operation, the output being based on the plurality of health data readings determined for a specified time period, and displaying at least one indicator for indicating the number of health data readings that are within a target range, the number of health data readings that are above the target range and the number of health data readings that are below the target range.

Figure 1A:
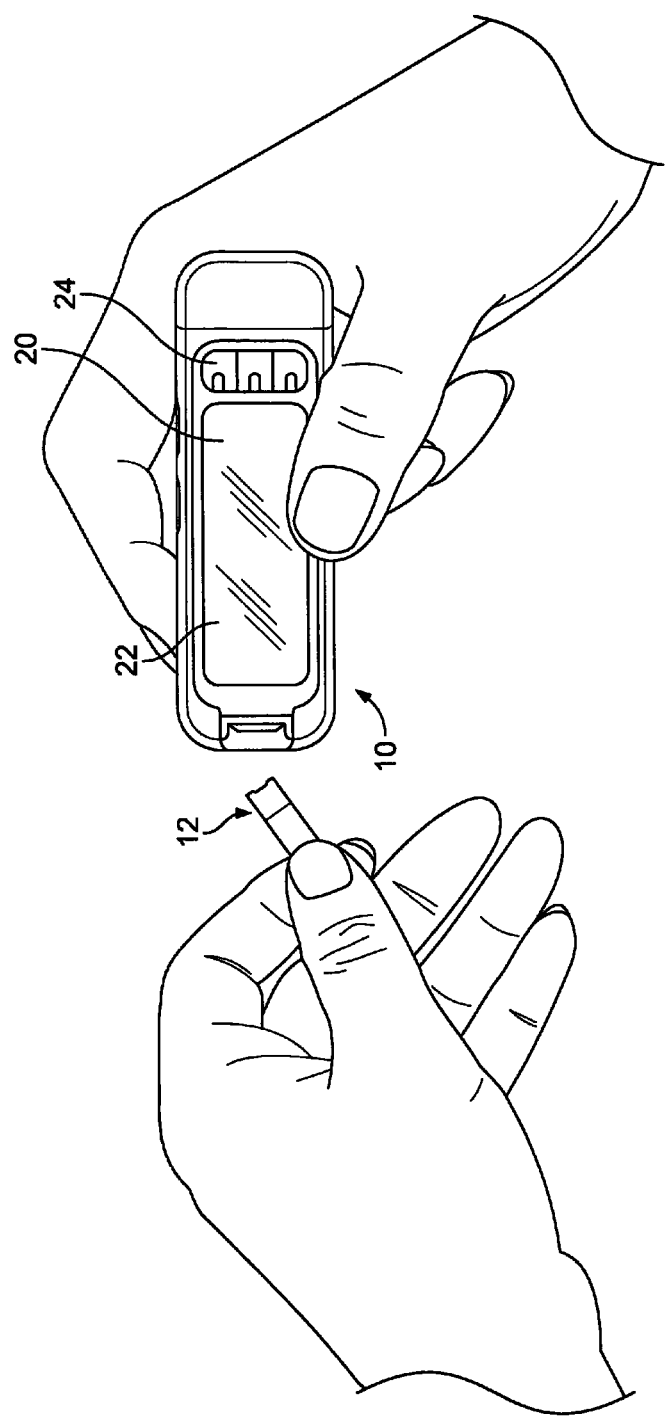
FIG. 1A illustrates a testing system having an interface for displaying health data.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATED EMBODIMENTS

Testing systems of the present invention provide information relating to health data. This health data may be collected, measured or input by a user. One example of such health data is an analyte concentration in a body fluid sample, such as glucose in a blood sample. Other types of health data may include heart rate measurements, blood pressure measurements, body temperature measurements, breathing measurements for chronic obstructive pulmonary disease (COPD) analysis, weight measurements for analyzing furosemide (LASIX®) use, and the like. For measurements that do not require analyte testing, the testing device 10 may monitor and analyze these types of health data and provide a user with the relevant information about the user's medical condition. Wherein the following description refers mainly to testing of analytes in fluid samples, it will be appreciated that other types of health data may be used with aspects of the present invention.

In some embodiments, a testing device as described herein may be employed in a larger health data management system that connects the testing device with other external processing devices, health care devices, and/or other devices/systems. The testing device may take advantage of the processing and user interface capabilities of such devices. For example, some functionalities may be better viewed on external processing devices if the size of the user interface on the testing device is too compact. Meanwhile, the health care devices may take advantage of the processing and user interface capabilities of the testing device. The interface between the testing device and the external devices may employ a wired communication protocol, such as the universal serial bus (USB) standard, or a wireless communication protocol, such as Bluetooth® technology.

For example, the testing device may be a blood glucose meter that interfaces with a processing device, such as a conventional personal computer (PC). Although the blood glucose meter may include advanced data processing and display features as described herein, users of the blood glucose meter may access more sophisticated analyses and presentations of blood glucose test data by connecting the blood glucose meter to a processing device that executes data-management software. For example, the software may be a product similar to WINGLUCOFACTS® Diabetes Management Software available from Bayer HealthCare LLC (Tarrytown, N.Y.). In another example, the testing device may be a blood glucose meter that interfaces with a health care device, such as a heart rate monitor, that transmits health data that can be combined with the data collected by the blood glucose meter itself.

Referring to FIG. 1A, one embodiment of a testing device 10 and a test sensor 12 is illustrated. The test sensor 12 is configured to receive a fluid sample which is analyzed using the testing device 10. Analytes that may be analyzed include glucose, lipid profiles (e.g., cholesterol, triglycerides, LDL and HDL), microalbumin, hemoglobin $A1_C$, fructose, lactate, or bilirubin. The analytes may be in, for example, a whole blood sample, a blood serum sample, a blood plasma sample, other body fluids like ISF (interstitial fluid) and urine, and non-body fluids.

Figure 1B:
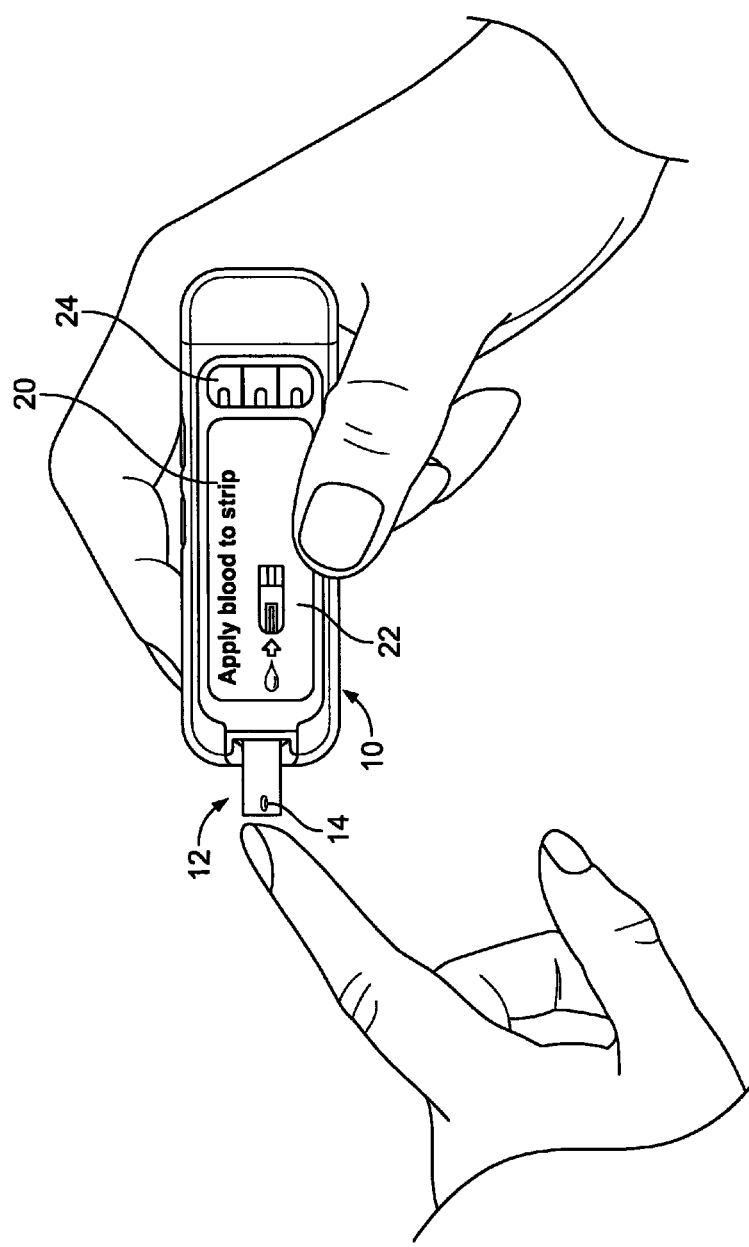
FIG. 1B illustrates the testing system of FIG. 1A showing a user applying a fluid sample to a test sensor.

As shown in FIG. 1B, the test sensor 12 includes a fluid-receiving area 14 for receiving a fluid sample. For example, a user may employ a lancet or a lancing device (not shown) to pierce a finger or other area of the body to produce the fluid sample at the skin surface. The user may then collect this fluid sample by placing the test sensor 12 into contact with the sample. The fluid-receiving area 14 may contain a reagent which reacts with the sample to indicate the concentration of an analyte in the sample.

In other embodiments, samples may be collected via a continuous glucose monitor (CGM) probe that is worn by the user and which collects samples of body fluid subcutaneously. Furthermore, different types of body-worn sensors and/or transmitters are contemplated as being usable with the present invention. For example, watches, arm bands, patches, earpieces, and other telemetry-based devices may be used to collect health data in connection with the embodiments disclosed herein. Such devices may be smaller, lighter and less invasive than traditional devices used for collecting health data.

The test sensor 12 may be an electrochemical test sensor. An electrochemical test sensor typically includes a plurality of electrodes and a fluid-receiving area that contains an enzyme. The fluid-receiving area includes a reagent for converting an analyte of interest (e.g., glucose) in a fluid sample (e.g., blood) into a chemical species that is electrochemically measurable, in terms of the electrical current it produces, by the components of the electrode pattern. The reagent typically contains an enzyme such as, for example, glucose oxidase, which reacts with the analyte and with an electron acceptor such as a ferricyanide salt to produce an electrochemically measurable species that can be detected by the electrodes. It is contemplated that other enzymes may be used to react with glucose such as glucose dehydrogenase. In general, the enzyme is selected to react with the desired analyte or analytes to be tested so as to assist in determining an analyte concentration of a fluid sample. If the concentration of another analyte is to be determined, an appropriate enzyme is selected to react with the analyte.

Alternatively, the test sensor 12 may be an optical test sensor. Optical test sensor systems may use techniques such as, for example, transmission spectroscopy, diffuse reflectance, or fluorescence spectroscopy for measuring the analyte concentration. An indicator reagent system and an analyte in a fluid sample are reacted to produce a chromatic reaction, as the reaction between the reagent and analyte causes the sample to change color. The degree of color change is indicative of the analyte concentration in the fluid. The color change of the sample is evaluated to measure the absorbance level of the transmitted light.

Some commercially available test sensors that may be used by the embodiments described herein include those that are available commercially from Bayer HealthCare LLC (Tarrytown, N.Y.). These test sensors include, but are not limited to, those used in the Ascensia® CONTOUR® blood glucose monitoring system, the Ascensia® BREEZE® and BREEZE®2 blood glucose monitoring system, and the Ascensia® Elite® and Elite® XL blood glucose monitoring system. It is contemplated that other test sensors, in addition to the ones listed above, may be incorporated into the methods and systems of the present invention.

As illustrated in FIG. 1B, the testing device 10 receives and engages the test sensor 12. The testing device 10 includes a reaction-detection system for measuring the concentration of analyte for the sample collected by the test sensor 12. As described above, the reaction-detection system may include contacts for the electrodes to detect the electrochemical reaction for an electrochemical test sensor. Alternatively, the reaction-detection system may include an optical detector to detect the chromatic reaction for an optical test sensor. To calculate the actual concentration of analyte from the electrochemical or chromatic reaction measured by the reaction-detection system and to generally control the procedure for testing the sample, the testing device 10 employs at least one processor (not shown), which typically executes programmed instructions according to a measurement algorithm. Data processed by the processor may be stored in a memory element.

The testing device 10 of FIG. 1B includes a user interface 20, which includes a display 22 and a user input device 24. The display 22 typically displays information regarding the test results, the testing procedure and/or information in response to signals input by the user, including text and images. The display 22 may be a graphic liquid crystal display (LCD), an organic light-emitting diode (OLED), segment LCD, or the like. The user input device 24 allows the user to interact with the testing device 10 and may include pushbuttons, soft keys, a scroll wheel, touch screen elements, or any combination thereof.

It is contemplated that the user interface 20 may provide a high-resolution, rich viewing display 22, which may present both static and moving text and images to the user. However, other types of displays, including, for example, lower resolution, monochromatic LCD displays, may be employed. In general, a range of display types, from a low-cost basic display to a fully functional display, may be employed. The display 22 may be of any suitable size. In some cases, the display 22 may cover one entire side of the testing device 10. Moreover, the display 22 may include a touchscreen. In addition, the user interface 20 may provide advanced graphical user display and audio capabilities available directly on the testing device 10 or via a communications interface with the testing device 10.

As described previously, the testing device 10 employs at least one processor that typically executes programmed instructions, as well as the user interface 20, which includes the display 22 to present information to the user, and input devices 24, such as pushbuttons, soft keys, a scroll wheel, touch screen elements, or any combination thereof, to enable interaction with the user. With such components, the testing device 10 generally controls the procedure for testing the sample and calculating the test results and for providing a plurality of user features. Certain of the user features of the testing device 10 may be available to the user via a hierarchical menu. The user is allowed to navigate through the hierarchical menu to access certain features of the testing device 10 that are described in more detail below. In some embodiments, the hierarchical menu has no more than four levels to provide quick and convenient access to the features of the device. For example, a user may operate a set of soft keys that corresponds to items in the hierarchical menu. In one embodiment, the testing device 10 provides three soft keys that are not dedicated to specific functions. Rather, the display 22 shows one set of three menu items and each of the soft keys is assigned to one of the menu items. Operating a soft key selects the corresponding menu item and either navigates the user to another level in the hierarchical menu or executes a particular function. Because the menu items are dynamically assigned to the soft keys, the user interface 20 does not require a separate key for each possible function, so many different functions are available even in a compact user interface 20. Further examples of such soft keys are described in detail herein below.

In some embodiments, to provide an easier and more intuitive process of entering information, the user interface 20 may prompt the user to input information or instructions into the testing device 10 relating to one or more features. More specifically, the user may be asked to respond to simple prompts or make menu selections to guide the user during operation of the testing device 10. One example of the user being prompted is shown in FIG. 1B in relation to an autologging feature. With this particular feature, once the test sensor 12 is inserted in the testing device 10, the user interface 20 provides instructions to the user to "APPLY BLOOD TO STRIP." The user interface 20 of FIG. 1B also pictorially displays a drip of blood with an arrow pointing to a test sensor to further guide the user.

Figure 1C:
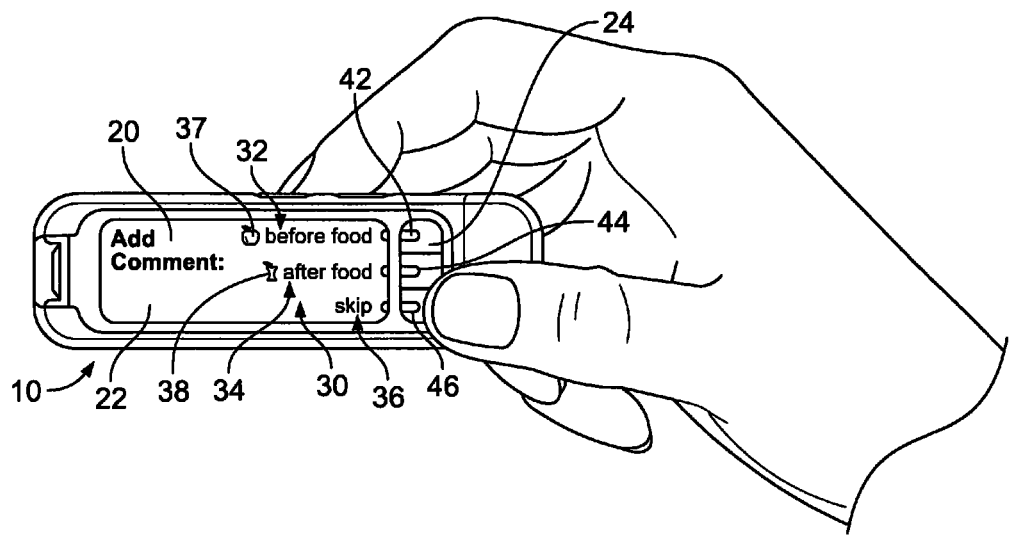
FIG. 1C illustrates information displayed on the user interface pertaining to an autologging feature.

Upon applying the blood to the strip, the user may be prompted to enter information into the testing device 10, as illustrated in FIG. 1C. Specifically, the user is prompted to "ADD COMMENT" via the user interface 20. To enter the requested information, the user may select from one or more user-selectable options displayed on the user interface 20. The user-selectable options may displayed adjacent to one or more input devices 24, such as soft keys, for receiving the user's input. In another example, the input devices 24 may also be used to retrieve information, such as test results, and to present the information on the display 12.

As noted above, FIGS. 1B and 1C illustrate certain prompts on the user interface 20 associated with an autologging feature, in particular for a diabetes-management system. These prompts immediately follow the application of blood onto the test sensor 12. Specifically, the user interface 20 prompts the user to press an input device 24 to select one of three user-selectable options 30 that correspond to the fluid sample being tested. Such information may be provided by inputting a single "click" of one of the soft keys on the input device 24. The particular user-selectable options associated with the autologging feature may be indicators, such as meal markers, that indicate when the fluid sample was taken in relation to when a meal has or has not been eaten. For example, one set of meal markers may include a "before food" marker (32), an "after food" marker (34) and a "skip" or "none" marker (36).

In the embodiment shown in FIG. 1C, the input device 24 includes three soft keys 42, 44, 46 which are assigned to each of the three user-selectable options 30. After a fluid sample is applied to the test sensor 12, a user is prompted during a certain time period to make a selection of one of the user-selectable options. Advantageously, the time period for receiving the user's selection may correspond to the time that it takes to perform the testing and calculations necessary to display the testing result. In some embodiments, the time period may be about 5 seconds. In other embodiments, the time period may be more or less than 5 seconds (i.e., 3 seconds, 10 seconds) and may depend on the type of test being performed.

This timing is an important feature as it allows for an opportunity to prompt the user to enter certain information, i.e., pre- and post-meal markers. Having the user input information relating to meals or other pertinent information occupies the user while he or she is waiting for the testing results. Furthermore, employing a testing system that takes, for example, 5 seconds to test the fluid sample generally will provide a higher level of accuracy than systems that may provide results in less than 5 seconds. Thus, it is desirable to have a testing system that provides sufficient time for the testing to occur and that also uses that time to gather additional beneficial information.

Ultimately, the information that is provided by the user may be categorized so that an evaluation of the data yields a more useful analysis for the user. Categorizing health data with meal markers, for example, helps the user to gain a better understanding of what values are being averaged and makes the data more actionable. In some embodiments, the categorization of information may be customized for different user groups, such as children or the elderly. Such categorization may be useful, for example, when taking averages of test results as certain averages, without more specific indicators, can mask information that may be useful in treating a disease.

Figure 1D:
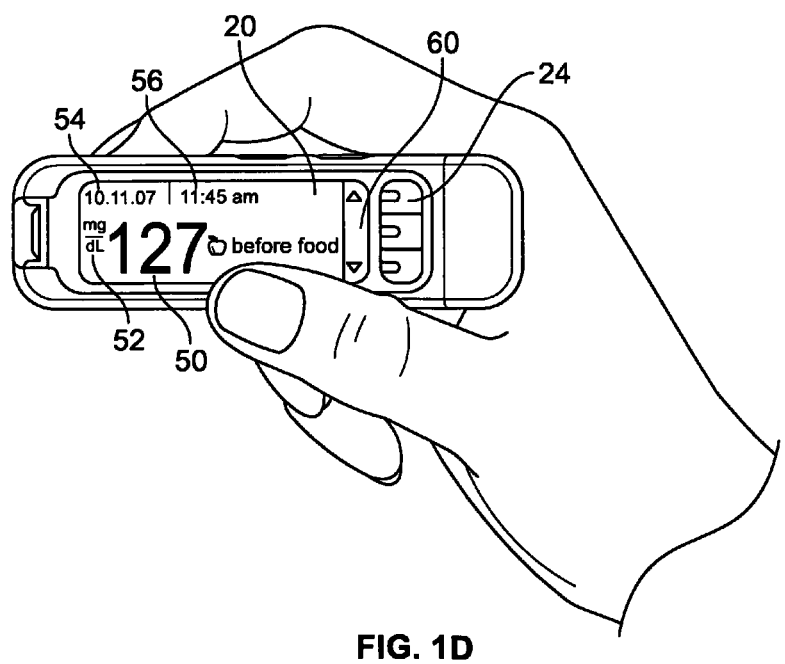
FIG. 1D illustrates information displayed on the user interface pertaining to a measurement of one type of health data.

After a selection is made by pressing one of the soft keys 42, 44, 46, a test result 50 is presented to the user, as shown in FIG. 1D. In this example, the test result 50 comprises a number indicative of a glucose concentration reading, along with the concentration units 52 and the date 54 and time 56. In this example, a concentration reading of 127 mg/dL is displayed, along with additional information pertaining to the meal marker. In some embodiments, the user can use a scroll function 60 to scroll back and forth among measurements performed by the testing device 10 to view prior testing results. This scroll function 60 is aligned with at least one soft key. Such prior testing results may be included in a log book feature that allows the user to identify dates, times and readings of prior concentration values.

Figure 4:
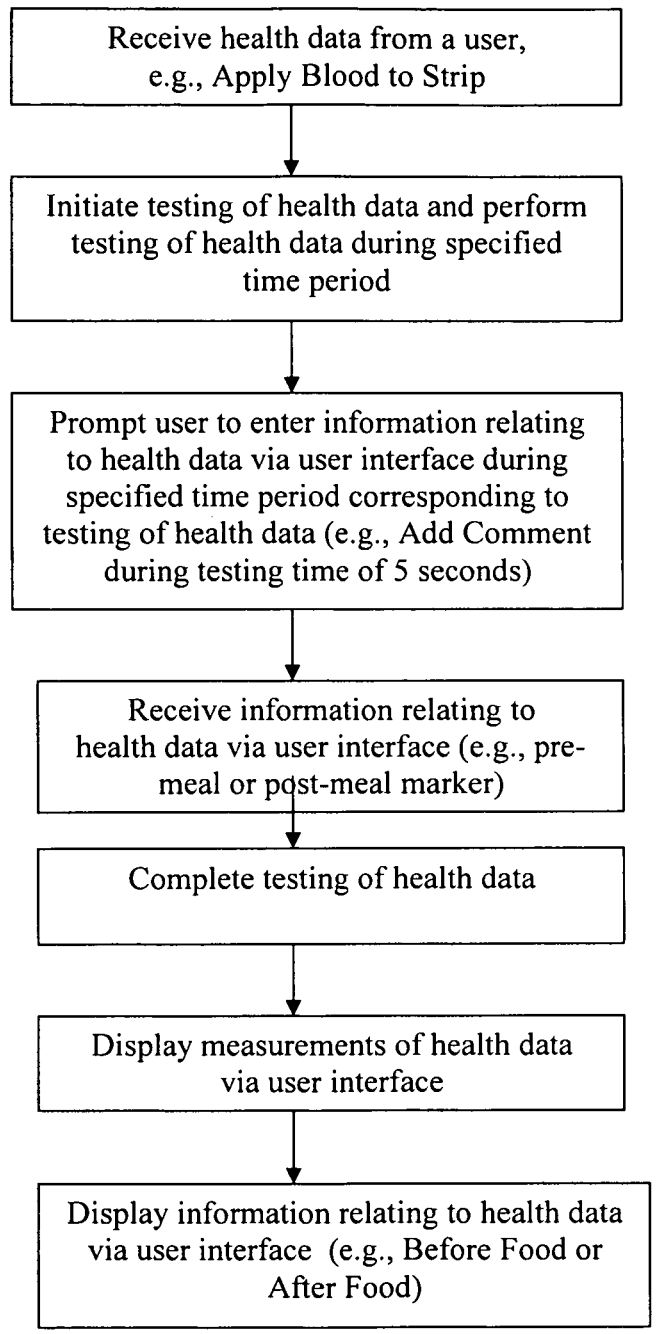
FIG. 4 illustrates a flow diagram pertaining to the autologging feature.

FIG. 4 provides a flow diagram illustrating generally the steps for entering information relating to the autologging feature and receiving the output via the user interface 20. Generally, upon receiving health data from the user, the testing of the health data is initiated and the testing is performed during a specified time period. The user is prompted to enter information relating to the health data via the user interface during the specified time period corresponding to the testing of health data, e.g., the user is prompted to add comments during a five second testing time. The user then inputs information relating to the health data via the user interface, e.g., by selecting a pre-meal or post-meal marker. Once the testing of the health data is completed, the measurements are displayed via the user interface. Additionally, the information relating to the health data that is input by the user may also be displayed, i.e., "before food" or "after food."

A primary advantage of the autologging feature is that it allows the user a way to record his or her readings as either pre-meal or post-meal data. The segregation of readings into pre/post meal categories allows users to better analyze the effects of food intake upon their blood glucose readings. In some embodiments, graphical elements 37, 38 can be used to make the selection process easier and to encourage users to mark their readings as pre- or post-meal during the testing routine. In this example, the pre-meal marker is identified with a whole apple and the post-meal marker is identified with an apple core; however, various graphical elements and/or wording may be used in connection with the autologging feature. In effect, the autologging feature automates the task of keeping a paper logbook by most individual with diabetes. The autologging feature also helps healthcare providers to draw their patients' attention to how food affects blood glucose readings.

In some circumstances where there is an immediate need for the testing results, it may be desirable to bypass the autologging feature in order to obtain the information relating to the analyte concentration reading and other measurements of health data without requiring that the user select one of the user-selectable options. This may be important where the user is having, for example, a hypoglycemic event that makes more critical the amount of time that is necessary to obtain the results from the testing device 10. The user may opt to bypass the autologging feature by selecting "skip" at the autologging feature, causing the testing results to be promptly displayed. Alternatively, the user may simply press a button that provides the results before the autologging feature is initiated. In some embodiments, the autologging feature may be initiated after the critical health data is displayed. Thus, the user may be given three opportunities to enter information pertaining to an autologging feature: during testing, after testing or after the "bypass" condition.

As mentioned above, other types of health data may be used with the present invention to provide important information to the user regarding the user's medical condition. Health data, such as heart rate measurements, blood pressure measurements, body temperature measurements, breathing measurements for COPD analysis, weight measurements for analyzing furosemide (LASIX®) use, and the like may be monitored, analyzed and reported to the user via the user interface 20. For example, the autologging feature may be used to provide a user with important details relating to a user's heart rate as it relates to one or more external factors, such as when the user recently ate, slept, exercised, etc.

Figure 2A:
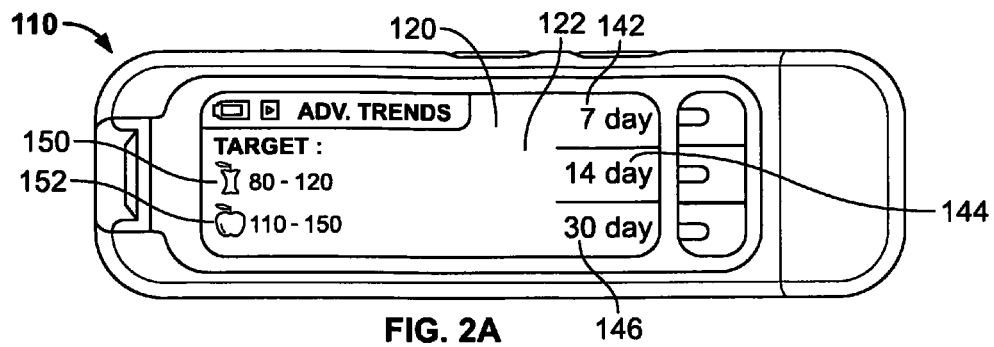
FIG. 2A illustrates information displayed on the user interface pertaining to a statistical operation performed by the testing system.

Other features providing different types of information can be displayed on a user interface 120. One such feature is shown in FIGS. 2A-2D, which depict a testing device 110 having a user interface 120 and display 122. According to this feature, a user is allowed to select, for example, a desired average reading from a list of selectable averages. For example, FIG. 2A illustrates a user interface 120 that provides a user with the option to select a "7-day" average 142, a "14-day" average 144 and a "30-day" average 146. The user interface 120 also provides information regarding target ranges for certain categories of readings, for example, a pre-meal target range 150 and a post-meal target range 152. These ranges 150, 152 may be default values or may be dependent on information input by the user. Thus, a user may be able to select from several averaging options: 7-day pre-meal, 7-day post-meal, 7-day overall average; 14-day pre-meal, 14-day post-meal, 14-day overall average; and 30-day pre-meal, 30-day post-meal and 30-day overall average. In some embodiments, a default average may include only the 14-day averages, for example. However, through connection to an external device, such as, for example, a PC, the user may tailor the averaging functionality via software embedded on the PC. The user may select other default settings and/or add additional functionalities relating to the autologging and averaging features.

Figure 2B:
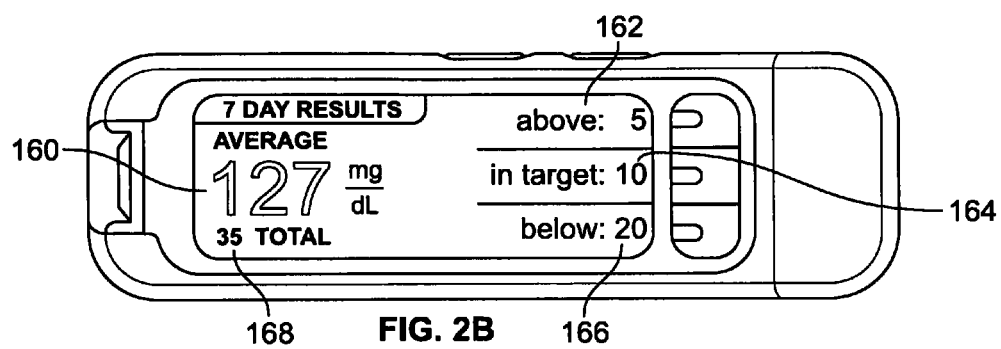
FIG. 2B illustrates information displayed on the user interface pertaining to an averaging feature according to one embodiment.
Figure 2C:
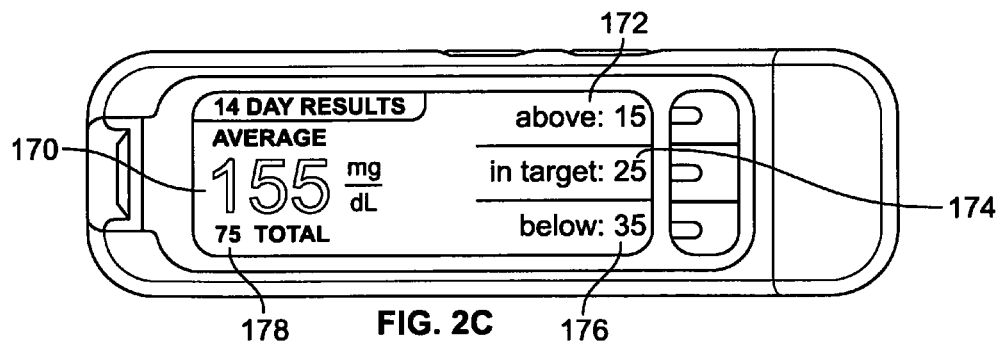
FIG. 2C illustrates information displayed on the user interface pertaining to an averaging feature according to another embodiment.
Figure 2D:
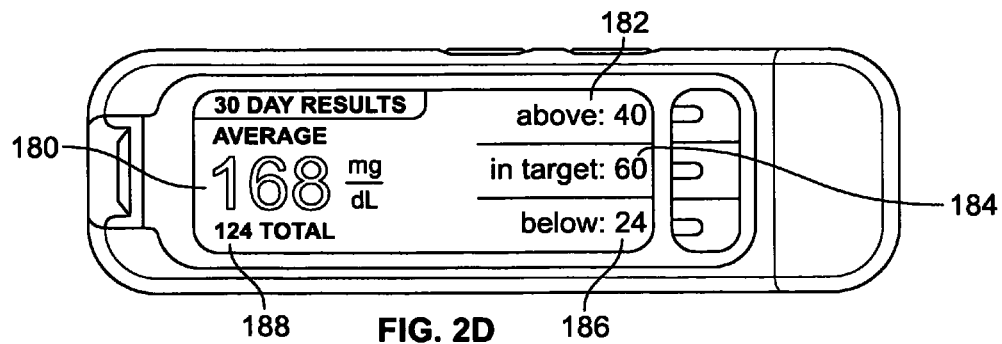
FIG. 2D illustrates information displayed on the user interface pertaining to an averaging feature according to yet another embodiment.

FIGS. 2B-2D illustrate the user interface 120 after a user has selected an average reading to be displayed. For example, when a user selects the "7 day" average 142, the user interface 120 displays the value 160 associated with the "7 day" average, e.g., 127 mg/dL, as shown in FIG. 2B. When a user selects the "14 day" average 144, the user interface 120 displays the value 170 associated with the "14 day" average, e.g., 155 mg/dL, as shown in FIG. 2C. When a user selects the "30 day" average 146, the user interface 120 displays the value 180 associated with the "30 day" average, e.g., 168 mg/dL. The user interface 120 may also indicate which of the readings is being displayed, i.e., "7 Day Results," to remind the user which averaging function the user selected.

In addition to displaying an average reading, the illustrated embodiments shown in FIGS. 2A-2D also reveal important information about the components of the average reading, e.g., "above," "below" and "in target." This additional useful information may be displayed to the user to indicate the number of readings that fall within the target range 164, 174, 184, the number of readings that fall above the target range 162, 172, 182 and the number of readings that fall below the target range, 166, 176, 186. Also, the total number of readings 168, 178, 188 that are used to provide the average value may be displayed for each of the specific averaging readings.

Figure 3:
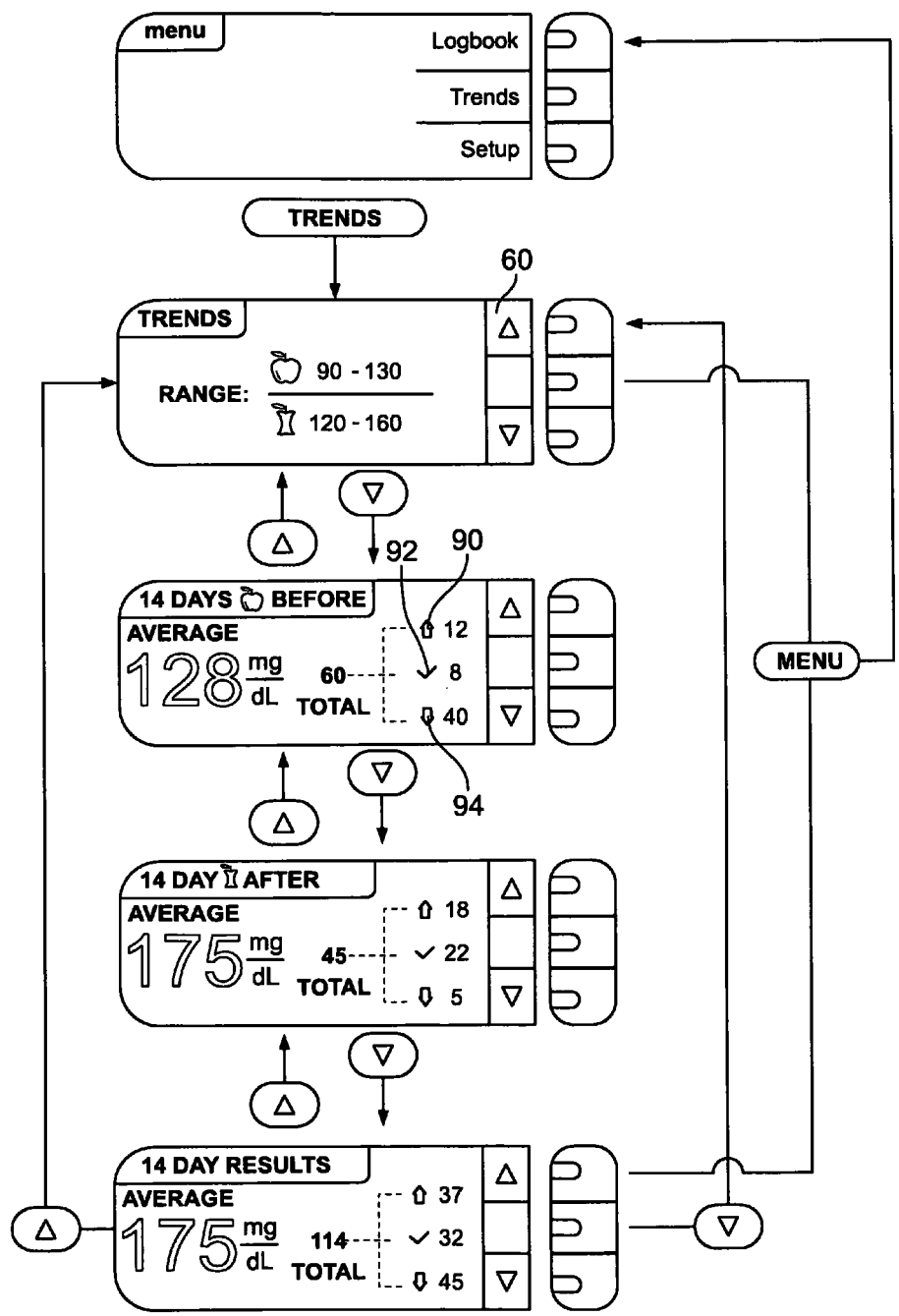
FIG. 3 illustrates information relating to a user work flow pertaining to an averaging feature according to a further embodiment.

In some embodiments, different colors may be associated and displayed with such a feature to assist in interpreting the testing results. As an example, red may be used to indicate readings that are below the target range, yellow may be used to indicate readings above the target range, and green may be used to indicate readings which are in the target range. In general, red may be used for a reading below the target range, because hypoglycemic events indicated by such a reading may present conditions which are more dangerous for a user. Furthermore, symbols may be used to pictorially represent the above, below and target ranges. For example, as shown in FIG. 3, an "up" arrow sign 90, a check mark 92 and a "down" arrow sign 94 may be placed next to a number of readings to represent pictorially the number of readings above, below and within target ranges, respectively. Such symbols may make it easier for user to identify the different categories and to understand the relationships between the components that make up the average value. FIG. 3 also depicts an example of the work flow of information relating to a menu of features that may be accessed by a user. For example, a user may select a "Trends" feature, which allows the user to scroll up and down between averages, such as pre-meal averages and post-meal averages. As noted above, the user can use the scroll function 60 (as depicted by the up and down triangles) to scroll between different types of averages, or other statistical operations, and between other types of information that may be provided in the Logbook, Trends and Setup functions.

This feature, which indicates the number of readings within and outside of a target range, provides useful information to the user, as well as a physician or nurse, to better reveal the trend of readings and to spot potentially troubling readings which a user may want to address. In addition, such a feature allows the user, physician or nurse to identify outlier data in testing results based on testing collected over several days, i.e., 7, 14 or 30 days. This information is presented in an intuitive and easily-understood manner so that a user can appreciate such results and make changes in the user's diet, exercise program, etc., which can help to reduce or eliminate the number and occurrence of readings outside of the target range.

Figure 5:
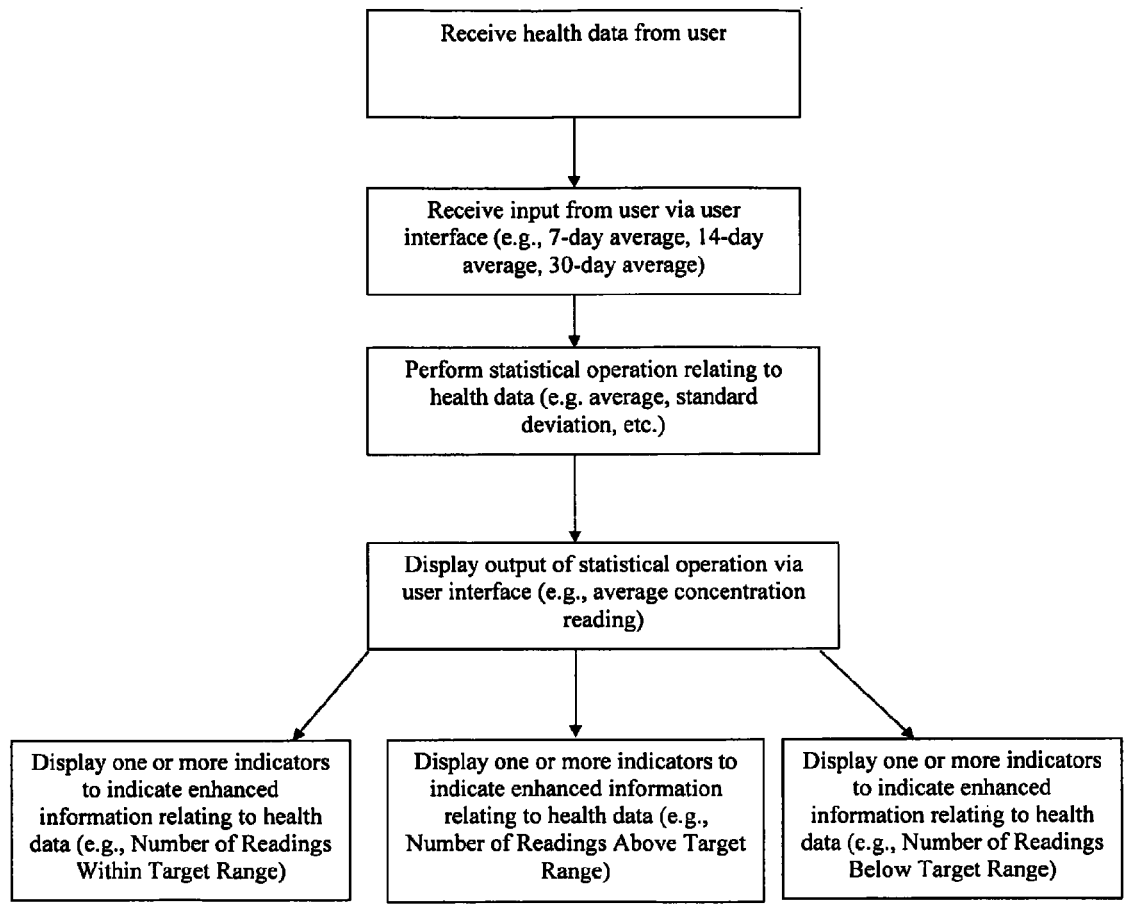
FIG. 5 illustrates a flow diagram pertaining to the averaging feature.

FIG. 5 provides a flow diagram illustrating generally the steps for entering information for performing a statistical operation and for receiving the output via the user interface 20. Generally, upon receiving health data from a user, the use inputs information via the user interface (e.g., selection of 7-day, 14-day or 30-day average). Depending on the information received from the user, a statistical operation, e.g., average, standard deviation, etc., is performed relating to the health data. The output of the statistical operation, e.g., a 7-day average concentration reading, is displayed via the user interface. Additional information or indicators may also be displayed to indicate enhanced information relating to the health data, e.g., the number of readings within, above or below the target range.

The user interface 120 allows users to further investigate the average reading and view the memory for more specific readings composing the average readings contained in a log book function. This may be achieved by scroll buttons or by selecting from a menu of options. For example, the user may opt to display the average value and target range for post-meal readings 150 or for pre-meal readings 152. This has the added benefit of further focusing a user's attention on eating habits and its relationship to the glucose concentration readings. This also allows the user to identify which readings contribute more to the number of readings outside of the target range and to allow the user to make adjustments to their meal routine. In general, the aspects of the embodiments described herein make the process of entering information about health data an easier, more intuitive process and provide the user with a better user experience. Furthermore, such embodiments will ultimately give the user more accurate and meaningful information about his or her condition and will encourage users to provide information in such a manner that it will become a routine part of their testing regimen.

In addition to the averaging of readings, other embodiments may also perform other types of statistical operations in addition to, or in lieu of, the averaging feature. For example, other types of statistical operations may include median values, mode values, standard deviations, confidence intervals, and the like. Furthermore, as mentioned above with respect to the autologging feature, other types of health data may be used with the statistical operations to provide important information to the user regarding a user's medical condition. Health data, such as heart rate, blood pressure, body temperature, breathing measurements, weight measurements and the like may be monitored, analyzed and reported to the user via the user interface 20, 120. For example, the statistical operations may be used to provide a user with important details relating to a user's heart rate based on values taken over a period of 7, 14 or 30 days. This allows the user to view such health data in the context of other readings taken over a particular time frame.

Other types of information may be entered by a user to add additional notes regarding the health data. For example, a user may be able to enter such notes as "gym day," "sick," "stress," "activity," "don't feel right," "traveling" and the like, to further identify the factors that may affect the measurement of the health data. Such labeling provides important information about lifestyle factors that enhance the value of the data to the users. Predefined notes may be provided for convenience, or the user may be able to customize notes through the user interface 20, 120. In other embodiments, the user may create notes through a separate software system and upload the notes to the testing device 10 through a communication interface.

In general, the user interface 20, 120 may present different information according to a variety of features to facilitate operation of the testing device 10. For example, the user interface 20, 120 may provide a power status indicator which shows the amount of power remaining in a rechargeable battery in the testing device 10. In addition, the user interface 20, 120 may display a countdown, rather than issuing an alarm, for testing times and may display a second clock for traveling. In other embodiments, the user interface 20, 120 may display a question mark for requested or missing information. Furthermore, the size of the displayed data may be modified depending on the type of data displayed and where in the testing process the data is being displayed. For example, the font size of a concentration reading may change to provide a larger-sized value to display to the user immediately after the testing is performed and then may modify the font size (i.e., make it smaller to fit on the display with additional information) of the value shortly thereafter. The changing of the size of the displayed data may also signal processing or logging of data.

As described previously, testing devices according to aspects of the present invention may include interfaces to connect to external systems or devices. The ability to communicate with external systems or devices may allow the testing device to download data and/or software. In some embodiments, for example, the testing device 10 may be field upgradeable to provide updates or patches to software on the testing device 10. The user interface 20, 120 may also be employed to facilitate the process of downloading data, such as field upgrades. For example, the user interface 20, 120 may communicate the availability of new or upgraded features via an icon on the display, when an external system signals the availability to the testing device 10. The user may then initiate, via the user interface, the transfer of the new or upgraded features. In some cases, the user may manage or control the transfer of such features by, for example, selecting particular features from a menu of features available for download.

The text and images provided on the user interface 20, 120 provide elements that enhance a user's experience with the device. In some embodiments, the display 22, 122 may have customizable attributes. For example, the display 22, 122 may have a customizable background, wallpaper, and/or animated screensaver. In some embodiments, users can customize the appearance of the user interface 20, 120 by installing custom pictures to display on the screen or by downloading display layouts made available by a manufacturer or an authorized third party.

In addition, user interfaces 20, 120 may allow information to be communicated to and from the user via audio signals. For example, input/output interfaces may include a speech synthesizer, MP3 playback, or the like, for communicating audio information to a user. Additionally, the input/output interfaces may also include a speech recognition mechanism to receive audio information from a user. In some embodiments, an audio interface (not shown) may be customized to use selected sounds, beeps, rings, tones, verbal messages, etc.

Furthermore, the user interfaces 20, 120 may provide access to various types of audio-visual content such as those associated with a PDA, smart cellular phone, etc. For example, a web browser available on the user interface 20, 120 may provide a further interface to functionality and features available through a connection to the Internet provided by a communication interface on the testing device 10. Additional user interface functionality may be provided by allowing e-mail functionality or text messaging functionality. Other user-selected audio-visual content may include music, movies, videos, video games, and the like.

In general, the user interface 20, 120 may be customizable to accommodate a user's personal preferences. For example, in some embodiments, the user interface 20, 120 may communicate in many languages. In one aspect, the data required to provide multi-language capability does not have to be stored locally, as users may download language files, via the communication interface, to customize the operation of their systems. Also, in another example, a flippable user interface may be provided on the testing device to accommodate right hand users and left hand users. The user interface may be digitally reoriented via a touch screen.

In yet other embodiments, as a convenience to the user, the last screen that was used by the user can be immediately displayed upon reactivating the testing device 10, 110. In other words, the testing device 10, 110 may store the state of the display, including prior information input by the user, so that user does not have to navigate through a menu of options. As described above, a testing device as described herein may be employed in a health management system that connects the testing device with an external processing device that executes a data-management software. Moreover, the testing device may take advantage of the user interface capabilities of the processing device. As such the ability to restore the state of the testing device 10, 110 can also be communicated to external processing device so that the data-management software starts at the most recent screen or function accessed by the user. For example, if the user most recently accessed a log book functionality on the testing device, the data-management software will automatically start at a corresponding log book function.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention.

What is claimed is:

1. A testing system comprising:
   a user interface including a display for displaying information relating to measurements of health data and an input device for receiving information from a user relating to the health data, the health data including data relating to an analyte concentration in a body fluid sample; and
   at least one processor providing an autologging feature unless the user selects an autologging bypass option,
   wherein the autologging feature provides the user with user-selectable options on the display and prompts the user to input meal information, the meal information being represented by the user-selectable options, the autologging feature prompting the user to input the meal information during a time period that begins when the testing system receives the body fluid sample and ends when the display displays a measurement of the analyte concentration, whereby, in order: (1) the testing system receives the body fluid sample to measure the analyte concentration; (2) after the testing system receives the body fluid sample, the autologging feature prompts the user to input the meal information; and (3) after the user inputs the meal information, the display displays the measurement of the analyte concentration, and
   wherein in response to the user selecting the autologging bypass option, the display displays the measurement of the analyte concentration on the display without requiring the user to input the meal information.

2. The testing system of claim 1, wherein the the meal information includes a before-food meal marker or an after-food meal marker.

3. The testing system of claim 1, wherein the health data is further related to a heart rate, a blood pressure, a body temperature, a breathing rate for COPD analysis, or a weight measurement for analyzing furosemide use.

4. The testing system of claim 1, wherein the user-selectable options are aligned on the display with a set of soft keys.

5. The testing system of claim 1, wherein the meal information provided by the user is displayed in connection with the measurement of the analyte concentration.

6. The testing system of claim 1, wherein the time period is about five seconds.

7. A method of providing a testing system, the method comprising the acts of:

providing the testing system having a user interface including a display for displaying information relating to measurements of health data and an input device for receiving information from a user relating to the health data, the health data including data relating to an analyte concentration in a body fluid sample;

in response to receiving the body fluid sample, executing, via at least one processor, the following acts via an autologging feature unless a user selects an autologging bypass option;

measuring the analyte concentration of the body fluid sample;

prompting the user to input meal information and receiving the meal information via the input device; and displaying the measurements of the the analyte concentration on the display, wherein the act of prompting occurs during a time period that begins when the testing system receives the body fluid sample and ends when the testing system displays a measurement of the analyte concentration on the display, wherein in response to the user selecting the autologging bypass option, the testing system displays the measurement of the analyte concentration on the display without requiring the user to input the meal information.

8. The method of claim 7, wherein the prompting of the user to input user information that corresponds to the health data includes displaying a plurality of user-selectable options.

9. The method of claim 7, wherein the meal information include a before-food meal marker and an after-food meal marker.

10. The method of claim 8, wherein the user-selectable options are aligned on the display with a set of soft keys.

11. The method of claim 7, wherein the time period is about five seconds.

12. The method of claim 7, wherein the analyte in the body fluid sample is glucose.

13. The method of claim 7, wherein the health data is further related to a heart rate, a blood pressure, a body temperature, a breathing rate for COPD analysis, or a weight measurement for analyzing furosemide use.

\* \* \* \* \*

UNITED STATES PATENT AND TRADEMARK OFFICE
CERTIFICATE OF CORRECTION

| | | |
|---|---|---|
| PATENT NO. | : 9,022,931 B2 | Page 1 of 1 |
| APPLICATION NO. | : 12/156043 | |
| DATED | : May 5, 2015 | |
| INVENTOR(S) | : Brauer et al. | |

It is certified that error appears in the above-identified patent and that said Letters Patent is hereby corrected as shown below:

IN THE CLAIMS

In Column 12, Line 56, in Claim 2, delete "the the" and insert -- the --, therefor.

In Column 13, Line 14, in Claim 7, delete "option;" and insert -- option: --, therefor.

In Column 13, Line 20, in Claim 7, delete "the the" and insert -- the --, therefor.

In Column 14, Line 11, in Claim 9, delete "information include" and insert -- information includes --, therefor.

Signed and Sealed this
Ninth Day of February, 2016

Michelle K. Lee
*Director of the United States Patent and Trademark Office*